(12) United States Patent
Mignon et al.

(10) Patent No.: US 9,789,039 B2
(45) Date of Patent: *Oct. 17, 2017

(54) OXIDATION DYEING PROCESS IMPLEMENTING A PRETREATMENT BASED ON A COMPOSITION RICH IN FATTY SUBSTANCES AND ON METAL CATALYSTS

(71) Applicant: L'OREAL, Paris (FR)

(72) Inventors: Marie Mignon, Paris (FR); Marie Giafferi, Villemomble (FR); Marie Crette, Paris (FR); Leïla Hercouet, Neuilly Plaisance (FR); Henri Samain, Bievres (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/899,621

(22) PCT Filed: Jun. 19, 2014

(86) PCT No.: PCT/EP2014/062928
§ 371 (c)(1),
(2) Date: Dec. 18, 2015

(87) PCT Pub. No.: WO2014/202712
PCT Pub. Date: Dec. 24, 2014

(65) Prior Publication Data
US 2016/0136068 A1    May 19, 2016

(30) Foreign Application Priority Data

Jun. 21, 2013    (FR) .................................... 13 55938

(51) Int. Cl.
| | | |
|---|---|---|
| *A61Q 5/10* | (2006.01) |
| *A61K 8/34* | (2006.01) |
| *A61K 8/31* | (2006.01) |
| *A61K 8/365* | (2006.01) |
| *A61K 8/19* | (2006.01) |
| *A61K 8/22* | (2006.01) |
| *A61K 8/41* | (2006.01) |
| *A61K 8/58* | (2006.01) |

(52) U.S. Cl.
CPC ................ *A61K 8/342* (2013.01); *A61K 8/19* (2013.01); *A61K 8/22* (2013.01); *A61K 8/31* (2013.01); *A61K 8/365* (2013.01); *A61K 8/411* (2013.01); *A61K 8/58* (2013.01); *A61Q 5/10* (2013.01); *A61K 2800/4324* (2013.01); *A61K 2800/884* (2013.01)

(58) Field of Classification Search
CPC .......... A61Q 5/10; A61K 8/411; A61K 8/342; A61K 8/22; A61K 8/31; A61K 8/365; A61K 8/19; A61K 2800/4324; A61K 2800/884

See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |
| 4,992,077 A | 2/1991 | Tennigkeit et al. |
| 5,061,289 A | 10/1991 | Clausen et al. |
| 5,380,340 A | 1/1995 | Neunhoeffer et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

Todd, Charles, et al., "Volatile Silicone Fluids for Cosmetic Formulations," Cosmetics and Toiletries, vol. 91, Jan. 1976, pp. 29-32.
International Search Report for PCT/EP2014/062928, mailed Oct. 6, 2014.
International Search Report for PCT/EP2014/062930, mailed Aug. 21, 2014.
English language Abstract for EP 0770375A1 (May 2, 1997).
English language Abstract for EP 1728500A1 (Dec. 6, 2006).
English language Abstract for FR 2886136A1 (Dec. 1, 2006).
English language Abstract for JP 02-019576A (Jan. 23, 1990).
English language Abstract for JP 05-163124A (Jun. 29, 1993).
Non-Final Office Action for co-pending U.S. Appl. No. 14/899,630 (Nov. 28, 2016).

*Primary Examiner* — Eisa Elhilo
(74) *Attorney, Agent, or Firm* — The Marbury Law Group, PLLC

(57) ABSTRACT

The present invention relates to a process for the oxidation dyeing of keratin fibers implementing: a) a step of pretreating said fibers by application to said fibers of a cosmetic composition (B) comprising: i) at least one fatty substance in an amount of greater than or equal to 10% by weight relative to the total weight of the composition (B); and ii) at least one metal catalyst; b) optionally a washing, rinsing, drying and/or rubbing-dry step; c) followed by a step of dyeing by application to said fibers of a cosmetic composition (A) comprising: i) at least one oxidation base, preferably chosen from para-phenylenediamines, bis(phenyl)alkylenediamines, para-aminophenols, ortho-aminophenols, heterocyclic bases preferably comprising at least two nitrogen atoms, and addition salts thereof; ii) optionally at least one coupler; and iii) at least one chemical oxidizing agent. The dyeing process makes it possible to significantly improve the dyeing properties of the coloration, in particular in terms of selectivity, of chromaticity, and of color intensity and uptake. The use of a composition which is rich in fatty substances, i.e. greater than 10%, and contains at least one catalyst pretreatment, before oxidation dyeing, allows a clear improvement in the dyeing properties, in particular in terms of dye uptake onto keratin fibers, of strength and of chromaticity and of selectivity of the color.

20 Claims, No Drawings

(56) References Cited

U.S. PATENT DOCUMENTS

| | | |
|---|---|---|
| 5,534,267 A | 7/1996 | Neunhoeffer et al. |
| 5,609,650 A | 3/1997 | Knuebel et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 9,173,821 B2 * | 11/2015 | Samain .................. A61K 8/31 |
| 2002/0050013 A1 | 5/2002 | Vidal et al. |
| 2003/0019051 A9 | 1/2003 | Vidal et al. |
| 2003/0066140 A1 * | 4/2003 | Bartolone .............. A61K 8/19 8/405 |
| 2008/0269352 A1 | 10/2008 | Falkowski et al. |
| 2010/0154140 A1 * | 6/2010 | Simonet ................. A61K 8/31 8/416 |
| 2010/0183536 A1 | 7/2010 | Ansmann et al. |
| 2010/0189665 A1 | 7/2010 | Dierker et al. |
| 2010/0189673 A1 | 7/2010 | Jackwerth et al. |
| 2010/0247588 A1 | 9/2010 | Hloucha et al. |
| 2010/0311627 A1 | 12/2010 | Hloucha et al. |
| 2011/0059032 A1 | 3/2011 | Dierker et al. |
| 2011/0142778 A1 | 6/2011 | Hloucha et al. |
| 2012/0110751 A1 * | 5/2012 | Blackburn ............. A61K 8/19 8/421 |
| 2013/0149272 A1 | 6/2013 | Hloucha et al. |

FOREIGN PATENT DOCUMENTS

| | | |
|---|---|---|
| DE | 4133957 A1 | 4/1993 |
| DE | 19543988 A1 | 5/1997 |
| EP | 0770375 A1 | 5/1997 |
| EP | 1728500 A1 | 12/2006 |
| FR | 2733749 A1 | 11/1996 |
| FR | 2801308 A1 | 5/2001 |
| FR | 2886136 A1 | 12/2006 |
| GB | 1026978 A | 4/1966 |
| GB | 1153196 A | 5/1969 |
| JP | 02-019576 A | 1/1990 |
| JP | 05-163124 A | 6/1993 |
| WO | 88/01162 A1 | 2/1988 |
| WO | 93/18738 A1 | 9/1993 |
| WO | 94/08969 A1 | 4/1994 |
| WO | 94/08970 A1 | 4/1994 |
| WO | 96/15765 A1 | 5/1996 |
| WO | 97/02008 A1 | 1/1997 |
| WO | 03/011237 A2 | 2/2003 |
| WO | 2006/013413 A1 | 2/2006 |
| WO | 2007/068371 A1 | 6/2007 |
| WO | 2008/155059 A2 | 12/2008 |
| WO | 2012/095397 A2 | 7/2012 |
| WO | 2012/175683 A2 | 12/2012 |
| WO | 2014/202714 A1 | 12/2014 |

* cited by examiner

OXIDATION DYEING PROCESS IMPLEMENTING A PRETREATMENT BASED ON A COMPOSITION RICH IN FATTY SUBSTANCES AND ON METAL CATALYSTS

CROSS REFERENCE TO RELATED APPLICATIONS

This is a national stage application of PCT/EP2014/062928, filed internationally on Jun. 19, 2014, which claims priority to French Application No. 1355938, which was filed on Jun. 21, 2013, both of which are incorporated by reference herein in their entireties.

The present invention relates to a process for the oxidation dyeing of keratin fibres implementing a pretreatment step based on a composition rich in fatty substances and comprising one or more metal catalyst(s).

Many people have sought for a long time to modify the colour of their hair and in particular to mask their grey hair.

It is known practice to obtain "permanent" or oxidation colourations with dyeing compositions containing oxidation dye precursors, which are generally known as oxidation bases, such as ortho- or para-phenylenediamines, ortho- or para-aminophenols and heterocyclic compounds. These oxidation bases are initially colourless or weakly coloured compounds, which, when combined with oxidizing products, may give rise to coloured compounds via a process of oxidative condensation.

It is also known that the shades obtained with these oxidation bases can be varied by combining them with couplers or colouration modifiers, the latter being chosen in particular from aromatic meta-diamines, meta-aminophenols, meta-diphenols and certain heterocyclic compounds, such as indole compounds. The variety of molecules used as oxidation bases and couplers allows a wide range of colours to be obtained.

The permanent dyeing process thus consists in applying, to the keratin fibres, bases or a mixture of bases and couplers with hydrogen peroxide ($H_2O_2$ or aqueous hydrogen peroxide solution), as oxidizing agent, in leaving to diffuse, and in then rinsing the fibres. The colourations which result therefrom have the advantage of being permanent, strong and resistant to external agents, in particular to light, bad weather, washing operations, perspiration and rubbing actions.

However, it is still sought to increase the efficiency of the reaction of the oxidation dyes used during this process in order to improve their uptake on keratin fibres. Indeed, such an improvement would make it possible in particular to decrease the contents of the oxidation dyes present in dyeing compositions, to reduce the leave-on time on keratin fibres and/or to use other dye families which have a weak dyeing capacity but which are capable of exhibiting a good toxicological profile, of providing new shades or of producing colourations which are resistant with respect to external agents such as light or shampoos.

In this regard, it has already been proposed to use cosmetic compositions containing metal catalysts during a dyeing process in order to accelerate the dye oxidation reaction and to improve the intensity of the colouration on the keratin fibres. However, the dyeing power obtained is still not entirely satisfactory and the colourations obtained are generally too selective, i.e. these colourations are not uniform along the keratin fibre.

There is therefore a real need to provide a process for dyeing keratin fibres which is carried out in the presence of an oxidizing agent and which does not have the drawbacks of the existing processes, i.e. which is capable of resulting in a satisfactory intensity of the oxidation dyes on the keratin fibres while at the same time resulting in relatively non-selective colourations.

Moreover, oxidation dyeing processes are known which implement a pretreatment step using a composition containing metal derivatives of manganese/cerium type and oxidation colourations. The pretreatment compositions generally consist of mixtures of water with alcohols (see, for example, WO 2003/011237, WO 97/022008), or in the presence of oil (WO 93/18738). Nevertheless, the colours obtained are not always satisfactory, in particular in terms of colour variety, coverage of grey hair, chromaticity, colouration intensity and/or selectivity.

This (these) aim(s) is (are) achieved by the present invention, one subject of which is a process for the oxidation dyeing of keratin fibres, in particular human keratin fibres such as the hair, implementing:
  a) a step of pretreating said fibres by application to said fibres of a cosmetic composition (B) comprising:
    i) at least one fatty substance preferably in an amount of greater than or equal to 10%, preferably greater than or equal to 25%, more preferentially in an amount of greater than or equal to 35% by weight relative to the total weight of the composition (B); and
    ii) at least one metal catalyst;
  b) optionally a washing, rinsing, drying and/or rubbing-dry step;
  c) followed by a step of dyeing by application to said fibres of a cosmetic composition (A) comprising:
    i) at least one oxidation base, preferably chosen from para-phenylenediamines, bis(phenyl)alkylenediamines, para-aminophenols, ortho-aminophenols, heterocyclic bases preferably comprising at least two nitrogen atoms, and addition salts thereof;
    ii) optionally at least one coupler; and
    iii) at least one chemical oxidizing agent.

The dyeing process makes it possible to significantly improve the dyeing properties of the colouration, in particular in terms of selectivity, i.e. colourations which are uniform along the keratin fibre, of chromaticity, and of colour intensity and uptake.

The use of a composition which is rich in fatty substances, i.e. greater than 10%, and contains at least one catalyst, as a pretreatment, before oxidation dyeing, allows a clear improvement in the dyeing properties, in particular in terms of dye uptake onto keratin fibres, of strength and of chromaticity and of selectivity of the colour.

Moreover, the dyeing process according to the invention makes it possible to improve the intensity of the colouration on the keratin fibres compared with a conventional dyeing process.

The present invention also relates to a multicompartment device comprising a first compartment containing a composition (B) as previously defined, a second compartment containing a composition (A') comprising i) one or more oxidation bases, preferably chosen from para-phenylenediamines, bis(phenyl)alkylenediamines, para-aminophenols, ortho-aminophenols, heterocyclic bases preferably comprising at least two nitrogen atoms, and addition salts thereof, ii) optionally one or more couplers and iv) optionally one or more organic or inorganic alkaline agents; and a third compartment containing a composition (C) comprising one or more oxidizing agents.

According to one particular embodiment, the device comprises a fourth compartment comprising a composition (D) comprising one or more fatty substances, said composition (D) to be mixed with the compositions (A') and (C), the fatty substance content being greater than or equal to 10% by weight relative to the total weight of the mixture of the compositions (A'), (C) and (D), the composition (A') or (C) possibly containing one or more fatty substances.

Other characteristics and advantages of the invention will emerge more clearly on reading the description and the examples that follow.

In that which follows and unless otherwise indicated, the limits of a range of values are included in this range.

The expression "at least one" is equivalent to the expression "one or more".

The composition (B) used in the invention comprises i) at least 10% of fatty substances and ii) at least one metal catalyst.

i) Fatty Substance(s):

The term "fatty substance" is intended to mean an organic compound that is insoluble in water at ordinary ambient temperature (25° C.) and at atmospheric pressure (760 mmHg) (solubility of less than 5%, preferably less than 1% and even more preferentially less than 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

These fatty substances are neither polyoxyethylenated nor polyglycerolated. They are different from fatty acids since salified fatty acids constitute soaps which are generally soluble in aqueous media.

The fatty substances are in particular chosen from $C_6$-$C_{16}$ hydrocarbons or hydrocarbons containing more than 16 carbon atoms and in particular alkanes, oils of animal origin, oils of plant origin, fluoro oils or glycerides of synthetic origin, fatty alcohols, fatty acid and/or fatty alcohol esters, non-silicone waxes, and silicones.

It is recalled that, for the purposes of the invention, the fatty alcohols, fatty esters and fatty acids more particularly contain one or more linear or branched, saturated or unsaturated hydrocarbon-based groups containing 6 to 30 carbon atoms, which is (are) optionally substituted, in particular with one or more hydroxyl groups (in particular 1 to 4). If they are unsaturated, these compounds may comprise one to three conjugated or non-conjugated carbon-carbon double bonds.

As regards the $C_6$-$C_{16}$ alkanes, they are linear or branched, and possibly cyclic. Examples that may be mentioned include hexane, dodecane, undecane, tridecane, and isoparaffins, for instance isohexadecane and isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

According to one particular embodiment, the fatty substance(s) used in the process of the invention is (are) chosen from volatile linear alkanes.

The term "one or more volatile linear alkane(s)" is intended to mean, without preference, "one or more volatile linear alkane oil(s)".

A volatile linear alkane that is suitable for the invention is liquid at ambient temperature (about 25° C.) and at atmospheric pressure (101 325 Pa or 760 mmHg).

The term "volatile linear alkane that is suitable for the invention" is intended to mean a linear alkane that can evaporate on contact with the skin in less than one hour, at ambient temperature (25° C.) and atmospheric pressure (101 325 Pa), which is liquid at ambient temperature, in particular having an evaporation rate ranging from 0.01 to 15 mg/cm$^2$/minute, at ambient temperature (25° C.) and atmospheric pressure (101 325 Pa).

Preferably, the volatile linear alkanes that are suitable for the invention have an evaporation rate ranging from 0.01 to 3.5 mg/cm$^2$/minute and better still from 0.01 to 1.5 mg/cm$^2$/minute, at ambient temperature (25° C.) and atmospheric pressure (101 325 Pa).

More preferably, the volatile linear alkanes that are suitable for the invention have an evaporation rate ranging from 0.01 to 0.8 mg/cm$^2$/minute, preferentially from 0.01 to 0.3 mg/cm$^2$/minute and even more preferentially from 0.01 to 0.12 mg/cm$^2$/minute, at ambient temperature (25° C.) and atmospheric pressure (101 325 Pa).

The evaporation rate of a volatile alkane in accordance with the invention (and more generally of a volatile solvent) may in particular be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m$^3$ which is temperature-regulated (25° C.) and hygrometry-regulated (50% relative humidity).

The volatile hydrocarbon-based solvent is allowed to evaporate freely, without stirring it, while providing ventilation by means of a fan (Papst-Motoren, reference 8550 N, rotating at 2700 rpm) placed in a vertical position above the crystallizing dish containing the volatile hydrocarbon-based solvent, the blades being directed towards the crystallizing dish, 20 cm away from the bottom of the crystallizing dish.

The weight of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of time (in minutes).

The evaporation rate is then calculated, which corresponds to the tangent to the origin of the curve obtained. The evaporation rates are expressed in mg of volatile solvent evaporated per unit of area (cm$^2$) and per unit of time (minutes).

According to one preferred embodiment, the volatile linear alkanes that are suitable for the invention have a non-zero vapour pressure (also known as saturation vapour pressure), at ambient temperature, in particular a vapour pressure ranging from 0.3 Pa to 6000 Pa.

Preferably, the volatile linear alkanes that are suitable for the invention have a vapour pressure ranging from 0.3 to 2000 Pa and better still from 0.3 to 1000 Pa, at ambient temperature (25° C.).

More preferably, the volatile linear alkanes that are suitable for the invention have a vapour pressure ranging from 0.4 to 600 Pa, preferentially from 1 to 200 Pa and even more preferentially from 3 to 60 Pa, at ambient temperature (25° C.).

According to one embodiment, a volatile linear alkane that is suitable for the invention may have a flash point that is in the range of from 30 to 120° C. and more particularly from 40 to 100° C. The flash point is in particular measured according to standard ISO 3679.

According to one embodiment, the volatile linear alkanes that are suitable for the invention may be linear alkanes comprising from 7 to 15 carbon atoms, preferably from 8 to 14 carbon atoms and better still from 9 to 14 carbon atoms.

More preferably, the volatile linear alkanes that are suitable for the invention may be linear alkanes comprising from 10 to 14 carbon atoms and even more preferentially from 11 to 14 carbon atoms.

A volatile linear alkane that is suitable for the invention may advantageously be of plant origin.

Preferably, the volatile linear alkane or the mixture of volatile linear alkanes present in the composition according to the invention comprises at least one $^{14}C$ (carbon-14) carbon isotope. In particular, the $^{14}C$ isotope may be present in a $^{14}C/^{12}C$ isotope ratio by number of greater than or equal to $1\times10^{-16}$, preferably greater than or equal to $1\times10^{-15}$, more preferably greater than or equal to $7.5\times10^{-14}$ and better still greater than or equal to $1.5\times10^{-13}$. Preferably, the $^{14}C/^{12}C$ ratio ranges from $6\times10^{-13}$ to $1.2\times10^{-12}$.

The amount of $^{14}C$ isotopes in the volatile linear alkane or the mixture of volatile linear alkanes may be determined via methods known to those skilled in the art such as the Libby compacting method, liquid scintillation spectrometry or accelerator mass spectrometry.

Such an alkane may be obtained, directly or in several steps, from a plant raw material, such as an oil, a butter, a wax, etc.

As examples of alkanes that are suitable for the invention, mention may be made of the alkanes described in patent applications WO 2007/068 371 and WO 2008/155 059. These alkanes are obtained from fatty alcohols, which are themselves obtained from coconut oil or palm oil.

As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14), and n-pentadecane (C15) and mixtures thereof. According to one particular embodiment, the volatile linear alkane is chosen from n-nonane, n-undecane, n-dodecane, n-tridecane and n-tetradecane, and mixtures thereof.

According to one preferred embodiment, mention may be made of mixtures of n-undecane (C11) and of n-tridecane (C13) obtained in Examples 1 and 2 of application WO 2008/155 059.

Mention may also be made of n-dodecane (C12) and n-tetradecane (C14) sold, respectively, under the references Parafol 12-97 and Parafol 14-97 by the company Sasol, and also mixtures thereof.

One embodiment consists in using only one volatile linear alkane.

Alternatively, a mixture of at least two different volatile linear alkanes, differing from each other by a carbon number n of at least 1, in particular differing from each other by a carbon number of 1 or 2, may be used.

According to one embodiment, a mixture of at least two different volatile linear alkanes comprising from 10 to 14 carbon atoms and differing from each other by a carbon number of at least 1, is used. Examples that may in particular be mentioned include mixtures of C10/C11, C11/C12 or C12/C13 volatile linear alkanes.

According to another embodiment, a mixture of at least two different volatile linear alkanes comprising from 10 to 14 carbon atoms and differing from each other by a carbon number of at least 2 is used. Examples that may in particular be mentioned include mixtures of C10/C12 or C12/C14 volatile linear alkanes, for an even carbon number n and the C11/C13 mixture for an odd carbon number n.

According to one preferred embodiment, a mixture of at least two different volatile linear alkanes comprising from 10 to 14 carbon atoms and differing from each other by a carbon number of at least 2, and in particular a mixture of C11/C13 volatile linear alkanes or a mixture of C12/C14 volatile linear alkanes, is used.

Other mixtures combining more than two volatile linear alkanes according to the invention, for instance a mixture of at least three different volatile linear alkanes comprising from 7 to 15 carbon atoms and differing from each other by a carbon number of at least 1, may be used in the invention.

In the case of mixtures of two volatile linear alkanes, said two volatile linear alkanes preferably represent more than 95% and better still more than 99% by weight of the mixture.

According to one particular embodiment of the invention, in a mixture of volatile linear alkanes, the volatile linear alkane having the smallest carbon number is predominant in the mixture.

According to another embodiment of the invention, a mixture of volatile linear alkanes in which the volatile linear alkane having the largest carbon number is predominant in the mixture is used.

As examples of mixtures that are suitable for the invention, mention may be made in particular of the following mixtures:
  from 50% to 90% by weight, preferably from 55% to 80% by weight and more preferentially from 60% to 75% by weight of Cn volatile linear alkane with n ranging from 7 to 15,
  from 10% to 50% by weight, preferably from 20% to 45% by weight and preferably from 24% to 40% by weight of Cn+x volatile linear alkane with x greater than or equal to 1, preferably x=1 or x=2, with n+x between 8 and 14, relative to the total weight of the alkanes in said mixture.

In particular, said mixture of volatile linear alkanes may also contain:
  less than 2% by weight and preferably less than 1% by weight of branched hydrocarbons,
  and/or less than 2% by weight and preferably less than 1% by weight of aromatic hydrocarbons,
  and/or less than 2% by weight, preferably less than 1% by weight and preferentially less than 0.1% by weight of unsaturated hydrocarbons,
  said percentages being expressed relative to the total weight of the mixture.

More particularly, the volatile linear alkanes that are suitable for the invention may be used in the form of an n-undecane/n-tridecane mixture.

In particular, use will be made of a mixture of volatile linear alkanes comprising:
  from 55% to 80% by weight and preferably from 60% to 75% by weight of C11 volatile linear alkane (n-undecane) and
  from 20% to 45% by weight and preferably from 24% to 40% by weight of C13 volatile linear alkane (n-tridecane),
  relative to the total weight of the alkanes in said mixture.

According to one particular embodiment, the mixture of alkanes is an n-undecane/n-tridecane mixture. In particular, such a mixture may be obtained according to Example 1 or Example 2 of application WO 2008/155 059.

According to another particular embodiment, the n-dodecane sold under the reference Parafol 12-97 by Sasol is used.

According to another particular embodiment, the n-tetradecane sold under the reference Parafol 14-97 by Sasol is used.

According to yet another embodiment, a mixture of n-dodecane and n-tetradecane is used.

Among the animal oils, mention may be made of perhydrosqualene.

Among the triglycerides of plant or synthetic origin, mention may be made of liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, jojoba oil, shea butter oil, caprylic/capric acid triglycerides, for instance those sold by the company Stéarineries Dubois or those sold under the names Miglyol® 810, 812 and 818 by the company Dynamit Nobel.

Among the fluoro oils, mention may be made of perfluoromethylcyclopentane and perfluoro-1,3-dimethylcyclohexane, sold under the names Flutec® PC1 and Flutec® PC3 by the company BNFL Fluorochemicals; perfluoro-1, 2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The liquid fatty alcohols that may be used in the cosmetic compositions of the invention are saturated or unsaturated, and linear or branched, and comprise from 6 to 30 carbon atoms and more particularly from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The wax(es) which may be used in the cosmetic compositions of the invention is (are) chosen in particular from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are in particular marine waxes such as the product sold by the company Sophim under the reference M82, and polyethylene waxes or polyolefin waxes in general.

As regards the fatty acid and/or fatty alcohol esters, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; cetyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" is intended to mean oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, glucose or methylglucose.

An example that may be mentioned is the product sold under the name Glucate® DO by the company Amerchol, which is a methylglucose dioleate.

Examples of esters or mixtures of esters of sugar of fatty acid that may also be mentioned include:

the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester-triester-polyester;

the sucrose monopalmitate/stearate-dipalmitate/stearate sold by the company Goldschmidt under the name Tegosoft® PSE.

The silicones that may be used in the cosmetic composition (A) of the present invention are volatile or non-volatile, cyclic, linear or branched silicones, which are unmodified or modified with organic groups, having a viscosity from $5 \times 10^{-6}$ to 2.5 m$^2$/s at 25° C., and preferably $1 \times 10^{-5}$ to 1 m$^2$/s.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's *Chemistry and Technology of Silicones* (1968), Academic Press. They may be volatile or nonvolatile.

When they are volatile, the silicones are more particularly chosen from those with a boiling point of between 60° C. and 260° C., and even more particularly from:

cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V 2 by Rhodia, decamethylcyclopentasiloxane sold under the name Volatile Silicone® 7158 by Union Carbide, and Silbione® 70045 V 5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

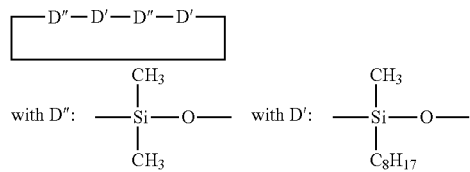

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane; (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone.

Silicones belonging to this category are also described in the article published in Cosmetics and Toiletries, Vol. 91, January 76, pp. 27-32, Todd & Byers, Volatile Silicone Fluids for Cosmetics.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:

mixtures formed from a hydroxy-terminated polydimethylsiloxane or dimethiconol (CTFA), and from a cyclic polydimethylsiloxane, also known as cyclomethicone (CTFA), such as the product Q2 1401 sold by the company Dow Corning;

mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and of a PDMS oil, such as the product SF 1236 from the company General Electric. The product SF 1236 is a mixture of a gum SE 30 defined above with a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$.

in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, and which are silicones of dimethyl/trimethylsiloxane structure. Mention may also be made of the trimethyl siloxysilicate-type resins sold in particular under the names X22-4914, X21-5034 and X21-5037 by the company Shin-Etsu.

The organomodified silicones that may be used in accordance with the invention are silicones as defined previously and comprising in their structure one or more organofunctional groups attached via a hydrocarbon-based group.

Besides the silicones described above, the organomodified silicones may be polydiarylsiloxanes, in particular polydiphenylsiloxanes, and polyalkylarylsiloxanes functionalized by the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:
 the Silbione® oils of the 70 641 series from Rhodia;
 the oils of the Rhodorsil® 70 633 and 763 series from Rhodia;
 the oil Dow Corning 556 Cosmetic Grade Fluid from Dow Corning;
 the silicones of the PK series from Bayer, such as the product PK20;
 the silicones of the PN and PH series from Bayer, such as the products PN1000 and PH1000;
 certain oils of the SF series from General Electric, such as SF 1023, SF 1154, SF 1250 and SF 1265.

Among the organomodified silicones, mention may be made of polyorganosiloxanes comprising:
 polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
 substituted or unsubstituted amine groups, such as the products sold under the names GP 4 Silicone Fluid and GP 7100 by the company Genesee or the products sold under the names Q2 8220 and Dow Corning 929 or 939 by the company Dow Corning. The substituted amine groups are, in particular, $C_1$-$C_4$ aminoalkyl groups;
 alkoxy groups such as the product sold under the name Silicone Copolymer F-755 by SWS Silicones, and Abil Wax® 2428, 2434 and 2440 by the company Goldschmidt. Preferably, the fatty substances do not comprise any $C_2$-$C_3$ oxyalkylene units or any glycerol units. Preferably, the fatty substances are not fatty acids and in particular salified fatty acids or soaps which are water-soluble compounds.

The fatty substances are advantageously chosen from $C_6$-$C_{16}$ hydrocarbons or hydrocarbons comprising more than 16 carbon atoms, and in particular alkanes, oils of plant origin, fatty alcohols, fatty acid and/or fatty alcohol esters, and silicones, or mixtures thereof.

Preferably, the fatty substance is an oil (a compound that is liquid at a temperature of 25° C. and at atmospheric pressure).

Preferably, the fatty substance is chosen from liquid petroleum jelly, $C_6$-$C_{16}$ alkanes, volatile linear alkanes, polydecenes, liquid fatty acid and/or fatty alcohol esters, and liquid fatty alcohols, or mixtures thereof. Better still, the fatty substance is chosen from liquid petroleum jelly, $C_6$-$C_{16}$ alkanes and polydecenes.

The fatty substances are present in a content of greater than 10% by weight, relative to the total weight of the cosmetic composition (B).

The composition (B) has a fatty substance content preferably ranging from 10% to 80% by weight, and even more particularly ranging from 20% to 75% by weight, better still from 25% to 70% by weight and quite particularly from 40% to 60% by weight relative to the total weight of the composition (B); preferentially, from 50% to 80% by weight relative to the total weight of the composition (B).

According to one advantageous variant of the invention, the process of the invention uses the composition (A) which has a fatty substance content preferably ranging from 10% to 90% by weight, and even more particularly from 20% to 80% by weight, better still from 20% to 50% by weight, relative to the total weight of the composition (A).

ii) Metal Catalyst(s)

The dyeing process according to the present invention uses in its composition (B) one or more metal catalysts.

Metal catalysts are compounds which comprise one or more metals in their structure.

The metals are chosen from transition metals and rare earth metals, and alloys thereof.

In particular, the metals are chosen from transition metals and rare earth metals.

Among the transition metals, mention may in particular be made of manganese, iron, cobalt, copper, zinc, platinum, nickel, titanium, silver, zirconium, chromium, molybdenum, tungsten, gold and vanadium, and among said metals, quite particularly manganese.

Among the transition metals, mention is preferably made of manganese, iron, cobalt, zinc, platinum, nickel, titanium, silver, zirconium, chromium, molybdenum, tungsten, gold and vanadium, and among said metals, quite preferably manganese.

Among the rare earth metals, mention may particularly be made of cerium.

Thus, the metal catalysts are in particular catalysts based on transition metals or on rare earth metals, and more particularly magnesium-based, vanadium-based or cerium-based catalysts.

The metal catalysts used may be chosen from metal salts, metal oxides and metal complexes, and mixtures thereof.

For the purposes of the present invention, the term "metal complexes" is intended to mean systems in which the metal ion, i.e. the central atom, is bonded to one or more electron donors, called ligands, via chemical bonds. As an example, mentioned may be made of porphyrins and phthalocyanines, which are in particular cationic.

Preferably, the metal catalysts used in the dyeing process are chosen from metal salts.

For the purposes of the present invention, the term "metal salts" is intended to mean the salts derived from the action of an acid on a metal.

Preferentially, the metal catalysts used in the dyeing process are chosen from transition metal salts, such as manganese salts, and rare earth metal salts, such as cerium salts, and also mixtures thereof.

The metal salts may be inorganic or organic salts.

According to one variant, the metal salts are inorganic and may be chosen from halides, carbonates, sulfates and phosphates, in particular optionally hydrated halides.

According to another preferred variant, the metal salts are in oxidation state II and have two (poly)hydroxy acid-derived ligands.

The term "(poly)hydroxy acid" is intended to mean any carboxylic acid which comprises a hydrocarbon-based chain which is linear or branched, and saturated or unsaturated, preferably saturated and/or linear, comprising from 1 to 10 carbon atoms and from 1 to 9 hydroxyl groups, and comprising from 1 to 4 carboxylic groups —C(O)—OH, at least one of said —C(O)—OH functions of which is in the carboxylate form —C(O)—O⁻ complexed with the metal atom, preferably Mn(II). More particularly, the metal salt is complexed with two carboxylate groups such as that of formula (I):

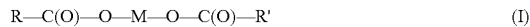

R—C(O)—O—M—O—C(O)—R'  (I)

and also the solvates thereof, such as the hydrates, and the enantiomers thereof, in which formula (I):

M represents a metal (II) or metal$^{2+}$ in oxidation state 2,
R and R', which may be identical or different, represent a ($C_1$-$C_6$)(poly)hydroxyalkyl group. The metal catalysts are particularly chosen from organic acid salts of transition metals, in particular of manganese, and inorganic salts of rare earth metals, in particular of cerium.

According to one particular embodiment of the invention, the manganese is not a manganese oxide, but a manganese salt The organic metal salts may be more particularly chosen from organic acid salts such as citrates, lactates, glycolates, gluconates, acetates, propionates, fumarates, oxalates and tartrates, in particular gluconates.

More preferentially, the metal catalysts are manganese gluconate and cerium chloride heptahydrate, in particular manganese gluconate.

Preferably, the metal catalyst(s) is (are) chosen from the compounds of formula (I) and more particularly represent(s) manganese gluconate.

The metal catalysts, when they are in the form of composition (B), may be present in a content ranging from 0.001% to 10% by weight, preferably in a content ranging from 0.001% to 1% by weight, better still ranging from 0.01% to 0.5% by weight relative to the total weight of the composition (B).

The composition (B) may exclusively contain the metal catalyst(s) combined with one or more fatty substances. According to another variant, this composition (B) contains compounds other than the metal catalyst(s), such as the additional ingredients, see "Additional ingredients or adjuvants" below.

This composition (B) may be anhydrous or aqueous, preferably aqueous.

The composition (A) used in the invention is a ready-to-use composition and comprises i) at least one oxidation base; ii) optionally at least one coupler; iii) at least one chemical oxidizing agent; and iv) optionally at least one organic or inorganic alkaline agent. The composition (A') of the device of the invention comprises the oxidation dyes i) and ii) as previously defined.

Oxidation Bases:

According to one particular embodiment of the invention, the oxidation base(s) is (are) preferably chosen from para-phenylenediamines, bis(phenyl)alkylenediamines, para-aminophenols, ortho-aminophenols, heterocyclic bases preferably comprising at least two nitrogen atoms, and addition salts thereof and/or solvates thereof; preferably the oxidation base(s) is (are) chosen from para-phenylenediamines, bis(phenyl)alkylenediamines.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Preference is particularly given, among the abovementioned para-phenylenediamines, to para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and the addition salts thereof with an acid.

Among the bis(phenyl)alkylenediamines, examples that may be mentioned include N,N'-bis(β-hydroxyethyl)-N,N'-bis(4'-aminophenyl)1,3-diaminopropanol, N,N'-bis(β-hydroxyethyl)-N,N'-bis(4'-aminophenyethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases, preference is given to those comprising at least two nitrogen atoms. More particularly, pyridine derivatives, pyrimidine derivatives and pyrazole derivatives are preferred.

Among the pyridine derivatives, examples that may be mentioned include the compounds described in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof, described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethy)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-(2-hydroxyethoxy)-3-aminopyrazolo[1,5-a]pyridine, 2-(4-methylpiperazinium-1-yl)-3-aminopyrazolo[1,5-a]pyridine, and the addition salts thereof.

Among the pyrimidine derivatives, mention may be made of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives, mention may be made of the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole, 3,5-diamino-4-(β-hydroxyethypamino-1-methylpyrazole, and the addition salts thereof. Use may also be made of 4,5-diamino-1-(β-methoxyethy)pyrazole.

A 4,5-diaminopyrazole and even more preferentially 4,5-diamino-1-(β-hydroxyethyl)pyrazole and/or a salt thereof will preferably be used.

Pyrazole derivatives that may also be mentioned include diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

As heterocyclic bases, use will preferentially be made of 4,5-diamino-1-(β-hydroxyethyl)pyrazole, 2,3-diamino-6,7-dihydro-1H,5H-pyrazolo[1,2-a]pyrazol-1-one, 2-(2-hydroxyethoxy)-3-aminopyrazolo[1,5-a]pyridine and 2-(4-methylpiperazinium-1-yl)-3-aminopyrazolo[1,5-a]pyridine; and/or an addition salt thereof.

Couplers:

According to one particular embodiment of the invention, the composition (C) comprises one or more couplers that are conventionally used for dyeing keratin fibres.

Preferably, the couplers are chosen from meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(6-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are in particular chosen from the addition salts with an acid, such as hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight, and preferably from 0.005% to 5% by weight relative to the total weight of the composition (A') and of the ready-to-use composition (A).

The content of coupler(s), if it (they) is (are) present, each advantageously represent from 0.001% to 10% by weight relative to the total weight of the composition, and preferably from 0.005% to 5% by weight relative to the total weight of the composition (A') and of the ready-to-use composition (A).

According to one particular embodiment of the invention, the composition (A) as previously defined also comprises one or more synthetic or natural direct dyes, chosen from ionic or non-ionic species, preferably cationic or non-ionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Mention may be made, among the natural direct dyes which can be used according to the invention, of lawsone, juglone, alizarin, purpurin, carminic acid, kermesic acid, purpurogallin, protocatechualdehyde, indigo, isatin, curcumin, spinulosin, apigenidin and orceins. Extracts or decoctions containing these natural dyes, and in particular henna-based poultices or extracts, may also be used.

When they are present, the direct dye(s) more particularly represent(s) from 0.001% to 10% by weight and preferably from 0.005% to 5% by weight relative to the total weight of the composition (A') or of the composition (A).

Chemical Oxidizing Agents:

More particularly, the chemical oxidizing agent(s) are chosen from hydrogen peroxide, urea peroxide, alkali metal bromates or ferricyanides, peroxygenated salts, for instance alkali metal or alkaline-earth metal persulfates, perborates, peracids and precursors thereof and percarbonates, and peracids and precursors thereof.

The oxidizing agent is preferably hydrogen peroxide.

This oxidizing agent advantageously consists of hydrogen peroxide, the concentration of which can range, more particularly from 0.1% to 50% by weight, more preferably still from 0.5% to 20% by weight and better still from 1% to 15% by weight, relative to the composition (C) or (D).

Additional Ingredients or Adjuvants:

According to one particular embodiment, the compositions (A), (A'), (B), (C) and/or (D) comprise one or more non-ionic, preferably oxyalkylenated, surfactants.

In accordance with one preferred embodiment of the invention, the surfactants are oxyalkylenated non-ionic surfactants and are chosen from oxyethylenated $C_8$-$C_{30}$ alcohols, and polyoxyethylenated esters of saturated or unsaturated, linear or branched $C_8$-$C_{30}$ acids and of sorbitol.

Preferably, the cosmetic compositions (A) and/or (C) comprise one or more non-ionic surfactants.

The surfactant content in the compositions (A) and/or (C) represents more particularly from 0.1% to 50% by weight and preferably from 0.5% to 30% by weight, relative to the weight of the composition under consideration.

The compositions (A), (B), (C) and/or (D) may also contain various adjuvants conventionally used in hair dyeing compositions, such as anionic, cationic, nonionic, amphoteric or zwitterionic polymers or mixtures thereof; inorganic thickeners, and in particular fillers such as clays or talc; organic thickeners/gelling agents with, in particular, anionic, cationic, nonionic and amphoteric polymeric associative thickeners other than the polymers previously mentioned; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of the composition under consideration.

According to one advantageous variant of the invention, the anhydrous composition (A) comprises one or more inorganic thickeners chosen from organophilic clays.

The organophilic clay can be chosen from montmorillonite, bentonite, hectorite, attapulgite, sepiolite and mixtures thereof. The clay is preferably a bentonite or a hectorite.

These clays can be modified with a chemical compound chosen from quaternary amines, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone 3, Bentone 38 and Bentone 38V by the company Rheox, Tixogel VP by the company United Catalyst and Claytone 34, Claytone 40 and Claytone XL by the company Southern Clay; stearalkonium bentonites, such as those sold under the names Bentone 27 by the company Rheox, Tixogel LG by the company United Catalyst and Claytone AF and Claytone APA by the company Southern Clay; quaternium-18/benzalkonium bentonites, such as those sold under the names Claytone HT and Claytone PS by the company Southern Clay; quaternium-18 hectorites, such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by the company Rheox, and Simagel M and Simagel SI 345 by the company Biophil.

When it is present, the inorganic thickener represents from 0.5% to 30% by weight relative to the weight of the composition. Advantageously, the composition is in the form of a gel, a cream or a foam.

The compositions (B) and/or (A) may be anhydrous or aqueous.

More particularly, for the purposes of the invention, the expression "anhydrous cosmetic composition" is intended to mean a cosmetic composition with a water content of less than 5% by weight, preferably less than 2% by weight and more preferably still less than 1% by weight relative to the weight of said composition. It should be noted that the water in question is more particularly bound water, such as water of crystallization in salts, or traces of water absorbed by the raw materials used in the production of the compositions according to the invention.

The term "aqueous composition" is intended to mean a composition comprising more than 5% by weight of water, preferably more than 10% by weight of water and more advantageously still more than 20% by weight of water.

Preferably, the cosmetic compositions (A) and/or (B) are aqueous compositions.

More preferentially still, the water concentration of the composition (A) or (B) may range from 10% to 90% and better still from 20% to 80% of the total weight of the composition.

The compositions (A), (A'), (B), (C) and/or (D) may optionally comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

The organic solvent(s), if it (they) is (are) present, represent(s) a content usually ranging from 1% to 40% and preferably ranging from 5% to 30% by weight relative to the weight of the composition containing it (them).

The pH of the compositions (A), (A'), (B), (C) and/or (D), if they are aqueous, ranges from 2 to 13.

For the compositions (A) and (B), the pH preferably ranges from 6.5 to 12 and better still from 8 to 12. The pH is adjusted using additional acidifying or alkaline agents, such as those mentioned below.

Basifying Agents:

Preferably, the compositions (A) and/or (B) comprise one or more organic or inorganic, preferably organic, basifying agents.

The basifying agent(s) can be inorganic or organic.

The inorganic basifying agent(s) is (are) preferably chosen from aqueous ammonia, alkali metal carbonates or bicarbonates such as sodium carbonate, potassium carbonate, sodium bicarbonate or potassium bicarbonate, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chains comprising more than ten carbon atoms.

The organic basifying agent(s) is (are) chosen, for example, from alkanolamines, oxyethylenated and/or oxypropylenated ethylenediamines, amino acids and the compounds of formula (III) below:

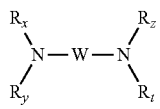
(III)

in which formula (III) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$, and $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (III) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$-$C_8$ alkyl groups bearing one or more hydroxyl radicals.

The organic amines chosen from alkanolamines such as monoalkanolamines, dialkanolamines or trialkanolamines comprising one to three identical or different $C_1$-$C_4$ hydroxyalkyl radicals are in particular suitable for carrying out the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that can be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (IV) below, and also the salts thereof:

(IV)

in which formula (IV) R represents a group chosen from:

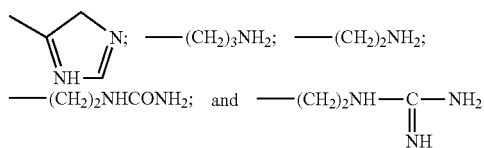

The compounds corresponding to the formula (IV) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that can be used in the present invention, mention may be made in particular of carnosine, anserine and balenine.

The organic amine may also be chosen from compounds comprising a guanidine function. As amines of this type that can be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in the composition of the invention is (are) chosen from aqueous ammonia, alkanolamines, amino acids in neutral or ionic form, in particular basic amino acids, and preferably corresponding to those of formula (III).

Even more preferentially, the basifying agent(s) is (are) chosen from aqueous ammonia and alkanolamines, most particularly monoethanolamine (MEA).

Better still, the basifying agent(s) is (are) chosen from alkanolamines, most particularly monoethanolamine (MEA).

By way of example, mention may be made of inorganic amines such as aqueous ammonia or organic amines. Organic amines chosen from alkanolamines such as monoalkanolamines, dialkanolamines or trialkanolamines comprising one to three identical or different $C_1$-$C_4$ hydroxyalkyl radicals, in particular monoethanolamine, are particularly suitable.

Preparation of the Ready-to-Use Composition (C):

As previously indicated, the ready-to-use composition (A) may result from the mixing of a composition (A') comprising i) one or more oxidation bases, ii) optionally one or more couplers, and of a composition (C) comprising one or more oxidizing agents as previously defined. The compositions (A') and (C) are preferably aqueous. They may in particular be in the form of direct or inverse emulsions.

They may also result from the mixing of three compositions, the first two being the compositions (A') and (C) above and the third composition being a composition (D) comprising at least one fatty substance as previously defined.

This composition (D) may be anhydrous or aqueous. It is preferably anhydrous.

Usually, the pH of the oxidizing composition (C), when it is aqueous, is acidic, i.e. less than 7.

Dyeing Processes:

In accordance with a first variant of the present invention, the composition (B) is applied to dry or wet keratin fibres. Then a dyeing composition (A) as previously defined is applied. According to one variant, the compositions (A') and (C) are mixed in order to produce the ready-to-use composition (A), then the mixture produced is applied to dry or wet keratin fibres.

There is preferably no intermediate rinsing.

The leave-on time of the composition (B) on the keratin fibres may range from 1 to 60 minutes, and is preferably from 10 minutes to 20 minutes.

In particular, the composition (B) is applied to the keratin fibres and left on for 10 minutes at ambient temperature.

Preferably, the composition (B) is sprayed onto the keratin fibres.

In addition, the dyeing composition (A) may be left in place on the keratin fibres for a time generally of about from 1 minute to 1 hour, preferably from 5 minutes to 40 minutes and preferably for 35 minutes.

The temperature during the process is conventionally between ambient temperature (between 15 and 25° C.) and 120° C. if a straightening iron is used, preferably between ambient temperature and 80° C., preferably from ambient temperature to 60° C. and better still from ambient temperature to 40° C.

According to one preferred embodiment, the composition (B) is applied to wet or dry keratin fibres, then the fibres are rinsed and rubbed dry with a towel. The composition (A) as previously defined is then applied, and then said fibres are optionally washed, rinsed and/or dried.

The drying step may last from 5 to 20 minutes, preferably from 5 to 15 minutes, and in particular lasts 10 minutes.

After the treatment, i.e. after the application of the composition (A) as previously defined, the human keratin fibres are preferably rinsed with water, optionally washed with a shampoo and then rinsed with water, before being dried under a hood at a temperature ranging from 50 to 80° C., or left to dry.

According to one particular embodiment of the invention, the process for dyeing keratin fibres is carried out in at least three successive steps:

firstly, of a composition (B) as previously defined comprising i) one or more metal catalysts chosen from transition metal salts, in particular organic acid salts of transition metals, and rare earth metal salts, in particular inorganic salts of rare earth metals, preferably manganese salts; ii) at least 10% preferably at least 35% of fatty substance(s), the fatty substance(s) preferentially being chosen from fatty substances that are liquid at ambient temperature and at atmospheric pressure, in particular chosen from liquid petroleum jelly, $C_6$-$C_{16}$ alkanes, polydecenes, liquid fatty acid and/or fatty alcohol esters, liquid fatty alcohols, or mixtures thereof;

and optionally iii) at least one basifying agent, in particular chosen from alkanolamines such as triethanolamine;

then, secondly, intermediate rinsing, and optionally rubbing dry preferably with a cloth or an absorbent paper, then, thirdly, a ready-to-use cosmetic composition (A) comprising i) at least one oxidation base chosen from para-phenylenediamines, bis(phenyl)alkylenediamines, para-aminophenols, ortho-aminophenols, heterocyclic bases preferably comprising at least two nitrogen atoms, and addition salts thereof; ii) optionally at least one coupler; and iii) at least one chemical oxidizing agent; and iv) particularly at least one basifying agent, preferably organic alkaline agent, in particular alkanolamines such as monoethanolamine (MEA) is applied.

Said ready-to-use composition (A) according to the invention is prepared just before its use by extemporaneous mixing of an oxidation dyeing composition (A') comprising at least one oxidation base; and ii) optionally at least one coupler, and of a composition comprising at least one chemical oxidizing agent (composition (C) as previously defined).

Finally, the invention relates to a multicompartment device comprising a first compartment containing a cosmetic composition (B) as previously defined, a second compartment containing a cosmetic composition (A') as previously defined, and a third compartment containing a composition (C) as previously defined. According to one particular embodiment, the device comprises a fourth compartment comprising a composition (D) comprising one or more fatty substances, said composition (D) to be mixed with the compositions (A') and/or (C), the fatty substance content being greater than or equal to 35% by weight relative to the total weight of the mixture of the compositions (A) to (D).

The device is suitable for implementing the dyeing process according to the present invention.

The evaluation of the coloration can be done visually or read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis. The lower the value of L, the darker or more intense the color. The higher the value of a*, the redder the shade; the higher the value of b*, the yellower the shade. The variation in coloring between the colored locks of natural white hair (NW) which is untreated (control) and after treatment or coloration are defined by ΔE*, corresponding to the colour uptake on keratin fibers, according to the following equation:

$$\Delta E^* = \sqrt{(L^* = L_o^*)^2 + (a^* - a_o^*)^2 + (b^* - b_o^*)^2}$$

In this equation, L*, a* and b* represent the values measured after dyeing the natural hair comprising 90% of white hairs and $L_0^*$, $a_0^*$ and $b_0^*$ represent the values measured for the untreated natural hair comprising 90% of white hairs.

The greater the value of ΔE, the greater the difference in color between the control locks and the dyed locks and the greater colour uptake is.

On the other hand for evaluating the selectivity of the color between the root and tip of the keratin fiber, measurement can be done on permed or sensibilised white hair (PW) and natural white hair, wherein the variation in coloring between the colored locks PW and the colored natural white hair are defined by ΔE*, corresponding to the selectivity of the colour, is calculated according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural hair comprising 90% of white hairs and $L_0^*$, $a_0^*$ and $b_0^*$ represent the values measured after dyeing the permed or sensibilised hair. The lowest ΔE*, the best homogeneity of the hair color.

If the light fastness is investigated, ΔE* is also calculated for the L0*, a0*, b0* and L*, a*, b* measured of the locks before and after exposure to the light, respectively.

Chromaticity in the CIE L*, a*, b* colorimetric system is calculated according to the following equation:

$$C^* = \sqrt{a^{*2} + b^{*2}}$$

The greater the value of C*, the greater the chromaticity is.

The examples that follow serve to illustrate the invention without, however, being limiting in nature.
The examples that follow serve to illustrate the invention without, however, being limiting in nature.

EXAMPLE 1

I. Compositions Tested
1/ Dyeing Process
The dyeing process consists of 3 steps:
Step 1: Application, with a brush, of 120 g of pretreatment per head, to dry hair, on volunteers having at least 70% grey hair. Leave-on time: 10 min at ambient temperature.
Step 2: Rinsing. Rubbing dry with an absorbent towel.
Step 3: Application of the mixture of the dyeing compositions (A) with a brush. 120 g overall. The leave-one time is 30 min at ambient temperature.
After this leave-on time, the locks are washed with Inoa Post shampoo, rinsed and then dried. The coloration obtained is evaluated blind by hairstylists.

2/ Preparation of the Pretreatments
Two Pretreatment Compositions are Prepared:

| Ingredients | (B) Invention* |
|---|---|
| Oxyethylenated lauryl alcohol (2 OE) | 2% |
| ($C_8/C_{10}/C_{12}/C_{14}$ 34/24/29/10) Alkyl Polyglucoside (1,4) as an aqueous solution at 53%, non protected (pH 11.5 using NaOH) | 2% |
| Acrylic polymer in emulsion | 4% |
| Hydrophobically modified inulin | 4% |
| Triethanolamine | 1% |
| 2-Octyldodecanol | 50% |
| Manganese gluconate•$2H_2O$ | 0.4% |
| Chlorhexidine digluconate in solution | 0.2% |
| 2-Phenoxyethanol | 0.7% |
| Deionized water (qs) | qs 100% |

*Amount: % in g for 100 g of composition (B)

3/ Preparation of the Dyeing Compositions:

| Composition (A') | |
|---|---|
| Ingredients | % in g |
| Ethylenediaminetetraacetic acid | 0.2% |
| Oxyethylenated oleyl alcohol (10 OE) | 1% |
| Cetyl palmitate | 2% |
| Vitamin C: L-Ascorbic acid as a fine powder | 0.12% |
| Oxyethylenated oleyl alcohol (20 OE) | 4% |
| Mixture of $C_{18}$ to $C_{24}$ linear alcohols ($C_{18}/C_{20}/C_{22}/C_{24}$: 7/58/30/6) alcohol content > 95% | 4.6% |
| Powdered sodium metabisulfite | 0.22% |
| Liquid petroleum jelly | 60% |
| Oxyethylenated decyl alcohol (5 OE) | 1.2% |
| Glycerol | 5% |
| 1-β-Hydroxyethyloxy-2,4-diaminobenzene dihydrochloride | 3.86% |
| Carboxyvinyl polymer synthesized in an ethyl acetate/cyclohexane mixture | 0.1% |
| Myristyl glycol ether of Oxyethylenated (60 OE) cetylstearyl ($C_{16}/C_{18}$) alcohol | 0.01% |
| Pure monoethanolamine | 6.3% |
| Deionized water | qs 100% |

| Composition C | |
|---|---|
| Ingredients | % in g |
| Poly[(dimethylimino)-1,3-propanediyl(dimethylimino)-1,6-hexanediyl dichloride] | 0.25% |
| Non-stabilized polydimethyldiallylammonium chloride at 40% in water | 0.5% |
| Diethylenetriaminepentaacetic acid, pentasodium salt as a 40% aqueous solution | 0.15% |
| Hydrogen peroxide as a 50% aqueous solution (200 vol. aqueous hydrogen peroxide solution) | 12% |
| Tetrasodium pyrophosphate•$10H_2O$ | 0.03% |
| Disodium tin hexahydroxide | 0.04% |
| Liquid petroleum jelly | 20% |
| Cetylstearyl alcohol (30/70 $C_{16}/C_{18}$) | 6% |
| Vitamin E: DL-alpha-Tocopherol | 0.1% |
| Oxyethylenated stearyl alcohol (20 OE) | 5% |
| Protected Oxyethylenated rapeseed acid amide (4 OE) | 1.3% |
| Glycerol | 0.5% |
| Phosphoric acid (pH) | qs pH |
| Deionized water (qs) | qs 100% |

At the time of use, the following are mixed: 60 g of the composition (A') and 60 g of the composition (C) (Inoa oxidizing agent, 20 vol). The mixture obtained, ready-to-use composition (C), has a pH of 9.8.

4/ Results Obtained

The evaluation was carried out on 3 volunteers having between 75-100% grey hair. A dark chestnut brown colour is obtained. The composition of the invention emerges as very efficient in terms of coverage of grey hair.

Example of Grading on a Volunteer:

| Volunteers | Grading scale: coverage of grey hair 5: no coverage, 6: medium coverage, 7: good coverage, 8: very good coverage Pretreatment with the composition of the invention (B) |
|---|---|
| 1 | 7.5 |
| 2 | 7.5 |
| 3 | 7 |

Demonstration Example 2

Pretreatment with the emulsion at 78.5% of oil vs aqueous-alcoholic gel pretreatment.

1/ Dyeing Process

It is the same process as for example 1.

The dyeing process consists of 3 steps.

Step 1: Application, with a brush, of 60 g of pretreatment per half-head (comparative on one side and invention on the other), to dry hair, on volunteers having at least 70% grey hair. Leave-on time: 10 min at ambient temperature.

Step 2: Rinsing. Rubbing dry with an absorbent towel.

Step 3: Application, with a brush, of the mixture of dyeing compositions. 120 g overall. The leave-on time is 30 min at ambient temperature.

After this leave-time, the locks are washed with Inoa Post shampoo, rinsed and then dried. The coloration obtained is evaluated blind by hairstylists.

2/ Preparation of the Pretreatments

Two Pretreatment Compositions are Prepared:

| Comparative composition: (B₂) | |
|---|---|
| Ingredients | % in g |
| Manganese gluconate•2H₂O | 0.4% |
| Denatured absolute ethyl alcohol | 50% |
| Hydroxyethylcellose MW: 1,300,000 | 1.5% |
| Deionized water (qs) | qs 100% |

| Composition of the invention (B') | |
|---|---|
| Ingredients | % in g |
| Oxyethylenated lauryl alcohol (2 OE) | 2% |
| (C₈/C₁₀/C₁₂/C₁₄: 34/24/29/10) Alkyl polyglucoside (1,4) in aqueous solution at 53%, non protected (pH 11.5 using NaOH) | 2% |
| SMDI/polyethylene glycol polymer bearing decyl end groups, as a water-glycol solution | 0.5% |
| Manganese gluconate•2H₂O | 0.4% |
| Liquid petroleum jelly | 78.5% |
| Deionized water (qs) | qs 100% |

3/ Preparation of the Dyeing Compositions

These are the same dyeing (A') and oxidizing (C) compositions as in Example 1.

4/ Results Obtained

This comparison was carried out on 3 volunteers having between 75-100% grey hair.

Example of Grading on a Volunteer:

| | Grading scale: Coverage of grey hair 5 : no coverage, 6: medium coverage, 7: good coverage, 8: very good coverage | |
|---|---|---|
| Volunteer | Pretreatment with the comparative composition (B₂) | Pretreatment with the composition of the invention (B') |
| 1 | 6.5 | 7.5 |
| 2 | 6.5 | 7 |
| 3 | 7 | 7.5 |

The process of the invention which uses as pretreatment the composition (B') or comprising at least one metal catalyst and an amount of fatty substance greater than or equal to 10%, of the invention, makes it possible to significantly improve the colouration of the hair, in particular in terms of coverage of grey hair.

The invention claimed is:

1. A process for the oxidation dyeing of keratin fibers, the process comprising:
    a) pretreating the fibers by applying to the fibers a first cosmetic composition comprising:
        i) at least one fatty substance in an amount of greater than or equal to about 10% by weight relative to the total weight of the first composition; and
        ii) at least one metal catalyst;
    b) optionally performing a washing, rinsing, drying, and/or rubbing-dry step; and
    c) dyeing the fibers by application to the fibers of a second cosmetic composition comprising:
        i) at least one oxidation base;
        ii) optionally at least one coupler; and
        iii) at least one chemical oxidizing agent.

2. The process according to claim 1, wherein the at least one fatty substance is chosen from $C_6$-$C_{16}$ hydrocarbons, hydrocarbons comprising more than 16 carbon atoms, alkanes, oils of plant origin, fatty alcohols, fatty acid esters, fatty alcohol esters, silicones, or combinations thereof.

3. The process according to claim 1, wherein the at least one fatty substance is chosen from oils, compounds that are liquid at a temperature of 25° C. and at atmospheric pressure, mineral oils, liquid petroleum jelly, $C_6$-$C_{16}$ alkanes, volatile linear alkanes, polydecenes, liquid fatty acid esters, fatty alcohol esters, liquid fatty alcohols, octyldodecanol, or combinations thereof.

4. The process according to claim 1, wherein the total amount of fatty substance in the first composition ranges from about 10% to about 80% by weight, relative to the total weight of the first composition.

5. The process according to claim 1, wherein the total amount of fatty substance in the first composition ranges from about 40% to about 60% by weight, relative to the total weight of the first composition.

6. The process according to claim 1, wherein the second composition comprises at least one fatty substance.

7. The process according to claim 6, wherein the total amount of fatty substance in the second composition ranges from about 10% to about 90% by weight, relative to the total weight of the second composition.

8. The process according to claim 1, wherein the at least one metal catalyst is chosen from metal salts, metal oxides, metal complexes, complexes of transition metal salts and rare earth metal salts, or combinations thereof.

9. The process according to claim 1, wherein the at least one metal catalyst is chosen from compounds including manganese, iron, cobalt, copper, zinc, platinum, nickel, titanium, silver, zirconium, chromium, molybdenum, tungsten, gold, vanadium, or combinations thereof.

10. The process according to claim 1, wherein the at least one metal catalyst is chosen from inorganic metal salts, halides, carbonates, sulfates, phosphates, hydrated halides, or combinations thereof.

11. The process according to claim 1, wherein the at least one metal catalyst is chosen from organic acid salts of transition metals, organic salts of manganese, inorganic salts of rare earth metals, inorganic salts of cerium, or combinations thereof.

12. The process according to claim 1, wherein the at least one metal catalyst is chosen from metal salts which possess a metal in oxidation state II and two (poly)hydroxy acid-derived ligands, metal salts that are complexed with two carboxylate groups, metal salts represented by formula (I):

solvates thereof, hydrates thereof, enantiomers thereof, or combinations thereof,
wherein in formula (I):
M represents a metal (II) or metal$^{2+}$ in oxidation state 2 or $Mn^{2+}$, and
R and R', which may be identical or different, represent a $(C_1$-$C_6)$(poly)hydroxyalkyl group.

13. The process according to claim 1, wherein the at least one metal catalyst is chosen from organic acid metal salts chosen from citrates, lactates, glycolates, gluconates, acetates, propionates, fumarates, oxalates, tartrates, or combinations thereof.

14. The process according to claim 1, comprising performing a rinsing and rubbing dry step.

15. The process according to claim 14, wherein the rubbing dry step is performed using a cloth or an absorbent paper.

16. The process according to claim 1, wherein the at least one oxidation base in the second composition is chosen from para-phenylenediamines, bis(phenyl)alkylenediamines, para-aminophenols, ortho-aminophenols, heterocyclic bases, heterocyclic bases comprising at least two nitrogen atoms, addition salts thereof, or combinations thereof.

17. The process according to claim 1, wherein the at least one chemical oxidizing agent in the second composition is chosen from hydrogen peroxide; urea peroxide; alkali metal bromates or ferricyanides; peroxygenated salts; alkali metal or alkaline-earth metal persulfates, perborates, peracids, or precursors thereof, or percarbonates, peracids, or precursors thereof.

18. The process according to claim 1, wherein at least one of the first compositions and the second composition further comprises at least one organic or inorganic basifying agent chosen from aqueous ammonia; alkali metal carbonates or bicarbonates; sodium carbonate; potassium carbonate; sodium bicarbonate; potassium bicarbonate; organic amines; alkanolamines; monoalkanolamines, dialkanolamines or trialkanolamines comprising one to three identical or different $C_1$-$C_4$ hydroxyalkyl radicals; oxyethylanated and/or oxypropylenated ethylenediamines; amino acids; the compounds represented by formula (III); or combinations thereof:

wherein in formula (III):
W is chosen from a divalent $C_1$-$C_6$ alkylene radical optionally substituted with at least one hydroxyl groups or a $C_1$-$C_6$ alkyl radical, and/or optionally interrupted with one or more heteroatoms such as O, or $NR_u$; and
$R_x$, $R_y$, $R_z$, $R_t$ and $R_u$, which may be identical or different, are chosen from a hydrogen atom or a $C_1$-$C_6$ alkyl, $C_1$-$C_6$ hydroxyalkyl, or $C_1$-$C_6$ amino alkyl radical.

19. A process for the oxidation dyeing of keratin fibers, the process comprising:
a) pretreating the fibers by applying to the fibers a first cosmetic composition comprising:
   i) at least one fatty substance chosen from fatty substances that are liquid at ambient temperature and at atmospheric pressure, liquid petroleum jelly, $C_6$-$C_{16}$ alkanes, polydecenes, liquid fatty acid esters, fatty alcohol esters, liquid fatty alcohols, or combinations thereof, wherein the total amount of fatty substance in the first composition is at least 35% by weight, relative to the total weight of the first composition;
   ii) at least one metal catalyst chosen from metal salts; metal oxides; metal complexes; complexes of transition metal salts and rare earth metal salts; compounds including manganese, iron, cobalt, copper, zinc, platinum, nickel, titanium, silver, zirconium, chromium, molybdenum, tungsten, gold, vanadium, or combinations thereof; inorganic metal salts, halides, carbonates, sulfates, phosphates, hydrated halides; organic acid salts of transition metals; organic salts of manganese; inorganic salts of rare earth metals; inorganic salts of cerium; organic acid metal salts chosen from citrates, lactates, glycolates, gluconates, acetates, propionates, fumarates, oxalates, tartrates; metal salts which possess a metal in oxidation state II and two (poly)hydroxy acid-derived ligands, metal salts that are complexed with two carboxylate groups, metal salts represented by formula (I):

solvates thereof, hydrates thereof, enantiomers thereof, or combinations thereof,
wherein in formula (I):
M represents a metal (II) or metal$^{2+}$ in oxidation state 2 or $Mn^{2+}$, and
R and R', which may be identical or different, represent a $(C_1$-$C_6)$(poly)hydroxyalkyl group; and
optionally at least one organic or inorganic basifying agent;
b) performing an intermediate rinsing and rubbing dry step; and
c) dyeing the fibers by application to the fibers of a ready-to-use cosmetic composition comprising:
   i) at least one oxidation base,
   ii) optionally at least one coupler;
   iii) at least one chemical oxidizing agent, and
   iv) at least one organic or inorganic basifying agent.

20. A multicompartment kit comprising:
a first compartment containing a first composition comprising:

at least one fatty substance in an amount of greater than or equal to about 10% by weight relative to the total weight of the first composition; and at least one metal catalyst;

a second compartment containing a second composition comprising:

at least one oxidation base; and optionally at least one coupler; and a third compartment containing a third composition comprising at least one chemical oxidizing agent.

* * * * *